United States Patent
Abrams et al.

[11] Patent Number: 5,467,868
[45] Date of Patent: Nov. 21, 1995

[54] OPHTHALMIC LENS PACKAGE

[75] Inventors: Richard Abrams; Russell J. Edwards; James A. Ebel; Darren S. Keene, all of Jacksonville, Fla.

[73] Assignee: Johnson & Johnson Vision Products, Inc., Jacksonville, Fla.

[21] Appl. No.: 174,580

[22] Filed: Dec. 28, 1993

Related U.S. Application Data

[63] Continuation of Ser. No. 995,607, Dec. 21, 1992, abandoned.

[51] Int. Cl.$^6$ .................................................. A45C 11/04
[52] U.S. Cl. ..................................... 206/5.1; 134/901
[58] Field of Search ................... 206/5.1; 134/901; D3/34

[56] References Cited

U.S. PATENT DOCUMENTS

| D. 210,248 | 2/1968 | Nissel | 206/5.1 X |
|---|---|---|---|
| 3,394,717 | 7/1968 | Hollinger | 206/5.1 |
| 3,414,117 | 12/1968 | Leeds | 134/901 X |
| 3,741,377 | 6/1973 | Kreller | 206/5.1 X |
| 3,780,918 | 12/1973 | Curtis | 206/5.1 X |
| 4,691,820 | 9/1987 | Martinez | 206/5.1 X |
| 5,080,839 | 1/1992 | Kindt-Larsen . | |
| 5,094,609 | 3/1992 | Kindt-Larsen . | |

FOREIGN PATENT DOCUMENTS

| 2057832 | 6/1992 | Canada . | |
|---|---|---|---|
| 82103214.1 | 11/1982 | European Pat. Off. . | |
| 3432002C2 | 11/1987 | Germany . | |
| 4736784 | 11/1969 | Japan | 206/5.1 |
| 2171812 | 9/1986 | United Kingdom . | |

OTHER PUBLICATIONS

The HighLighter System Diagram (existed prior to Dec. 21, 1991, as admitted by Applicant).

*Primary Examiner*—Bryon P. Gehman

[57] ABSTRACT

An ophthalmic lens package for inspection, sterilization, and delivery of the lens having a substantial planar first surface with a concave bowl, the bowl having a radius of curvature larger than the radius of the lens placed inside the bowl allowing the lens to center and settle in the middle of the bowl. About the bowl is an annular sealing area, preferably a planar annulus raised above the first planar surface away from the bowl, circumferentially about the circular boundary of the first planar surface and the concave bowl. The package is hermetically sealed along the sealing area with a sealing sheet substantially parallel with the first planar surface and covering the concave bowl. The package is constructed of a non-nucleated polymer so that when water is placed in the bowl, the polymer surface is sufficiently wettable to substantially flatten the water meniscus in the center and thereby eliminate associated optical aberrations, permitting undistorted in-package inspection.

22 Claims, 2 Drawing Sheets

OPHTHALMIC LENS PACKAGE

This is a continuation, of application Ser. No. 07/995,607, filed on Dec. 21, 1992, now abandoned.

BACKGROUND OF THE INVENTION

This invention relates to an efficient package for the storage and delivery as well as possible inspection of an ophthalmic lens, in particular ophthalmic lenses such as hydrogel contact lenses whose structures are comprised of a substantial portion of water, although the package is also suitable for the inspection of other small, high precision ophthalmic lenses such as intraocular lenses.

As the ophthalmic lens industry has grown, such packaging has become a larger expenditure of material and financial resources, particularly with regard to contact lenses that are provided for a periodic, frequent replacement. The number of lenses that need to be produced and, therefore, packaged has increased dramatically.

In addition, with the increasing number of lenses produced that in turn need to be inspected, it is desirable to have an ophthalmic lens package that can also serve as an inspection vehicle allowing the lens to be inspected in-package and avoiding the extra steps, cost, complications and equipment associated with transferring the lens to a special inspection vehicle then to a package.

Prior art ophthalmic lens packages have had, as a rule, ease of handling without particular concern for the size of the package or the ability to inspect the lens in the package. In particular, the package described in U.S. Pat. No. 4,691,820 to Martinez is a molded blister package comprising a base portion having a cavity surrounded by an outstanding flange and a cover sheet sealed to the flange to enclose the cavity. A portion of the side wall of the cavity is inclined to form a ramp to the flange for easy removal of the lens by sliding it up and out of the cavity along the inclined surface.

Similar designs are shown in U.S. Pat. Des. Nos. 299,085 and 305,478 granted to Martinez and Lamb et al., respectively.

While convenient and suitable for its purpose, the prior art packages do not meet the requirements of minimizing the amount of material utilized, allowing high speed filling and sealing of the packages, achieving easy handling and opening by the ultimate consumer and making possible, if desired, in package inspection of the lens by use of an appropriate lighting source and viewing apparatus.

It is, therefore, an object of the present invention to provide a package which allows easy filling of the package with the ophthalmic lens and processing water, removal of the processing water and addition of the appropriate water solution and which can be sealed quickly and easily. The bowl of the package must, therefore, be deep enough to contain sufficient solution to cover the lens.

Another object of the invention is easy handling and opening by the ultimate consumer. The bowl of the package must, for this requirement, be wide enough to allow a finger to be inserted into the bowl to extract the lens. The package must also be easy to open and handle during lens removal by the consumer.

It is a further object of the present invention to provide an ophthalmic lens package which permits in-package inspection of the lens, if desired. The bowl of the package, to allow this objective, must be shallow enough to maximize the focal length of the water-filled package.

Another object of the invention is to provide a package wherein the lens consistently rest at the center of the package to allow for in-package inspection.

It is a final objective of the present invention to accomplish the above with minimal use of materials while retaining desirable handling characteristics.

SUMMARY OF THE INVENTION

These and other objects are attained by use of a package for ophthalmic lenses having a substantial planar first surface with a concave bowl formed therein, the bowl having a radius of curvature sufficiently small to cause the lens to center, but larger than the radius of the lens placed inside the bowl allowing the lens to center and settle in the middle of the bowl. About the bowl is an annular sealing area, preferably a planar annulus raised above the first planar surface away from the concave bowl circumferentially about the circular boundary of the first planar surface and the concave bowl. The package is hermetically sealed along the sealing area with a sealing sheet substantially parallel with the first planar surface and Covering the concave bowl. In the preferred embodiment of the present invention, there is a second planar surface at a non-zero angle from an edge of the first planar surface in the same direction of the concave bowl extending for approximately the same distance from the first planar surface as the concave bowl in order that the package will rest level. The package is constructed of a non-nucleated polymer so that when water is placed in the bowl, the polymer surface is sufficiently wettable to substantially flatten the water meniscus in the center and thereby eliminate associated optical aberrations, permitting undistorted in-package inspection. The package of the present invention has a sufficiently smooth surface (a roughness of 800 grit or higher a #2 SPI-SPE Polish) which allows isotropic, that is uniform lighting of the lens, yet provides a coefficient of static friction sufficient to retain the lens while processing water is removed.

DESCRIPTION OF THE PREFERRED EMBODIMENT

Figure 1:
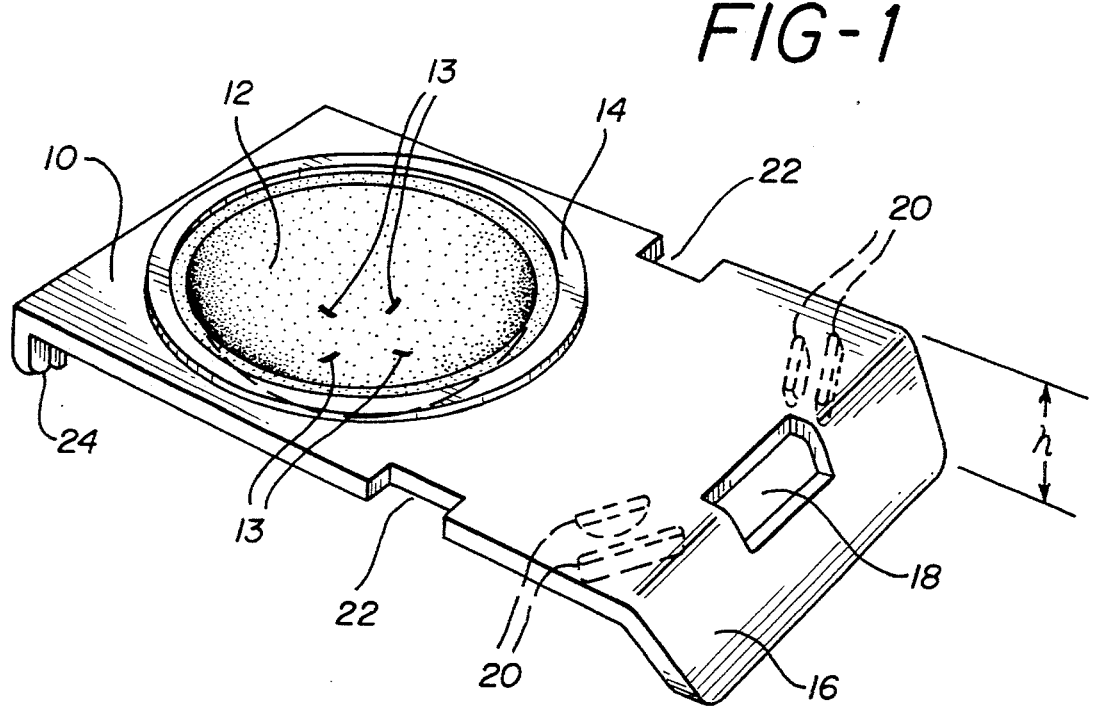
FIG. 1 is an isometric view of the package of the present invention showing substantially the top portion.

Referring now to FIG. 1, shown is a package for an ophthalmic lens having a substantially planar first surface 10. Formed within this planar first surface is hemispherical bowl 12 which is concave when viewed from the top of the package. Within bowl 12 are contained a plurality of ribs 13. These ribs are located near, but off-center of the bowl. Each rib 13 is 0.5 mm long and 0.025 mm wide. The ribs are located 3.0 mm from the center of the package, 6.0 mm from the ends of its collinear partner.

Figure 2:
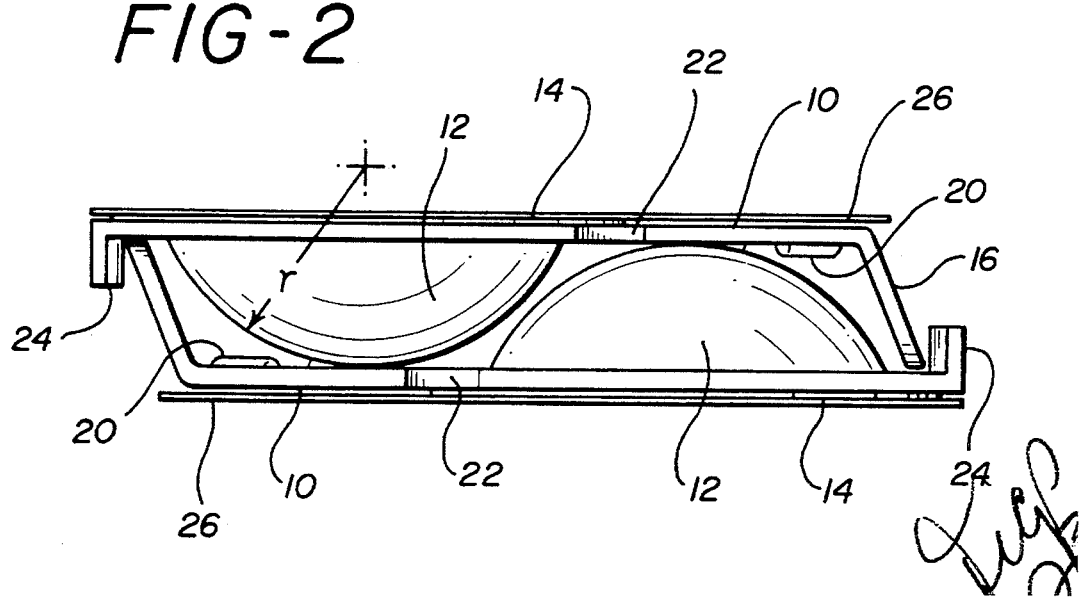
FIG. 2 is a side view of two packages of the present invention showing the manner in which the two packages may be nested together.
Figure 3:
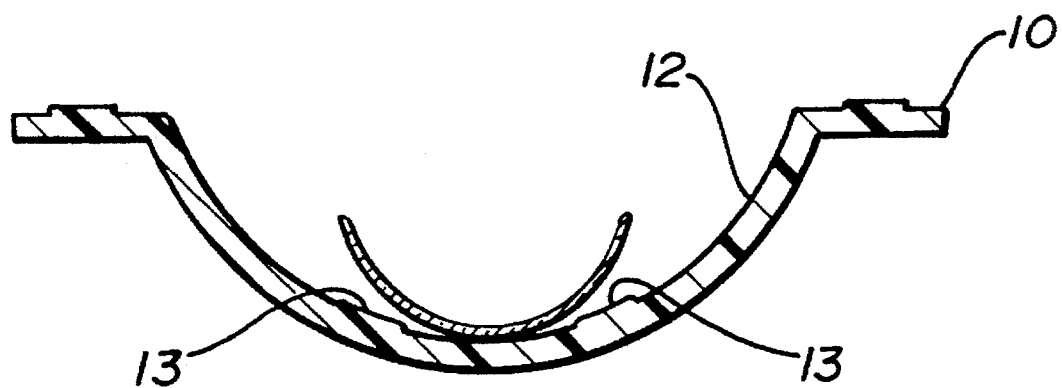
FIG. 3 is a cutaway view of the package.

Referring to FIG. 2, the radius of the spherical bowl designated in this drawing as "r" is such that the radius of curvature of the bowl is larger than the radius of curvature of the ophthalmic lens to be placed therein.

The ophthalmic lens is a hydrophilic contact lens having a front radius of curvature of between 7.0 mm and 11.0 mm, depending on the optical power, with about 8.50 mm being a typical value. In such a case the bowl would have a radius of curvature greater than 8.50 millimeters, but sufficiently small preferably less than 12 millimeters in order to cause proper lens centering by gravity.

In the present embodiment, the preferred radius of curvature for the package bowl is 9.5 mm. In 30 test runs using packages from 9.5 mm to 12.0 mm moving at 75 mm/sec, this dimension package had the smallest standard deviation of lens displacement from center, as measured on a CCD video camera, summarized as follows:

| Package Radius of Curvature (mm) | One Standard Deviation (pixels) | Three Standard Deviation (pixels) |
| --- | --- | --- |
| 9.5 | 5.0 | 15.1 |
| 10.0 | 20.5 | 61.6 |
| 11.0 | 13.5 | 40.5 |
| 11.5 | 33.0 | 99.1 |
| 12.0 | 26.4 | 79.3 |

The radius of curvature of the bowl must be greater than the radius of curvature of the contact lens placed therein, however, in order to have the contact lens touch the bowl only at one point and not have line or surface contact between the lens and the bowl which would create additional friction between the lens and the bowl and inhibit the movement of the lens to the center of the bowl.

As an additional constraint, if the radius of curvature of the bowl is much greater than 12 millimeters, the contact lens would move freely meeting the above criterion of having strictly point contact, but would fail to center within the bowl because of the flatness of the bowl.

In addition, the interior surface of the bowl must have the appropriate roughness, preferably less than 800 grit. This roughness is sufficiently limited to allow the lens to fall to the center of the bowl in water and to allow the lens to slide against the interior surface for removal with the finger.

The package contains near the center of the bowl raised ribs 13. The lens floats over the ribs during centering of the lens in the package, but does not make contact with these ribs when centered, touching only the package center at a point. The ribs retain the lens during removal of the deionized water during the packaging process.

Referring back to FIG. 1, there is also provided a sealing area 14 located circumferentially about the circular boundary of the first planar surface 10 and the concave bowl 12. This sealing area is preferably a planar annulus as shown in element 14 raised above the first planar surface away from the concave bowl.

Also there is provided a sealing sheet (not shown) such as aluminum foil laminated between two sheets of polyester such as that manufactured by Alusuisse of Geneva, Switzerland. This sealing sheet is placed substantially parallel with the first planar surface to cover the concave bowl thereby forming a cavity which encloses the lens and fluid that is placed within the bowl 12.

The raised annular planar surface 14 provides an area for heat sealing the plastic coated foil over a controlled surface area thereby insuring a hermetic seal yet providing easy removal by the ultimate user.

In the preferred embodiment, the package further comprises a second planar surface 16 which extends from an edge of the first planar surface 10 at a non-zero angle in the direction of the concave bowl 12. Preferably, the second planar surface extends substantially the same distance, h, from the first planar surface as does the apex of the concave bowl so that the package, when placed on a flat, level resting surface remains level, and does not tip nor spill its contents. The depth of the bowl, h, is thus less than the diameter of the lens contained therein, thus inhibiting inversion of the lens by containing it between the bowl and covering.

To allow for easy grasping of the sealing sheet (not shown), when being removed, a portion of the first planar surface and the second planar surface is removed to create a notched section 18. This notch permits the ultimate consumer to easily peal back the foil up to the area sealed against the raised annular sealing area 14, and break the hermetic seal therebetween.

The package may also include a plurality of projections 20 substantially in a normal direction from the first planar surface and near an edge to provide additional assistance in gripping the package during opening.

The package may also include in the first planar surface a means for indicating the presence and position of the package in a production line such as notches 22. These notches can be used in conjunction with a locating means such as a light source and photodiode to precisely indicate when a lens has moved into a particular position along a production line.

It is also desirable to carefully locate the package in any type of production line carrying means such as a pallet. This may be done by means of locating tabs 24; one of which is shown in FIG. 1, the other opposite the tab shown is located unseen in this figure underneath the first planar surface 10. It is readily obvious to one skilled in the art the way in which the tabs can be used to lock an ophthalmic lens package into a pallet that is moving along a production line. In addition, it is possible to use notches 22 alone or in conjunction with locating tabs 24 to securely locate the package in a production line carrying means such as a pallet, in addition to using notches 22 as a means for indicating the presence and position of the package.

A more detailed description of the preferred embodiment of the lens transport system and pallet system with illumination triggering are given in copending U.S. application Ser. Nos. 994,249 filed Dec. 21, 1992 for Ophthalmic Lens Inspection System and Method. Ser. No. 994,242, filed Dec. 21, 1992 for Pallet for Receiving and Transporting Ophthalmic Lens Container.

As stated above, one of the major objectives of the present invention is to permit, if desired, the in-package inspection of the ophthalmic lens contained therein. This inspection would preferably take place before the sealing sheet is placed over the bowl 12.

The method of capturing an lens image with a camera and determining whether a lens is acceptable once an image is captured by the camera and reduced to digital data is described in copending U.S. application Ser. No. 993,756 filed Dec. 21, 1992 for Ophthalmic Lens Inspection Method and Apparatus.

In the preferred embodiment, therefore, the bowl 12, and preferably the whole package, is constructed of a non-nucleated polymer such as polypropylene Exxon PP1105. Because this material is non-nucleated, it is sufficiently wettable, and it substantially flattens the meniscus associated with the water in the center of the container. Because the surface of the water contained within bowl 12 does not form a significant meniscus and is therefore, substantially flat, there are no optical aberrations associated with the top surface of the water.

This material, as would be preferred of any other material used in the present invention, is made translucent or sufficiently transparent so that light passes through the bowl isotropically, that is with minimal diffusion, absorption, concentration by the surfaces, or granularity.

As can be appreciated by one skilled in the art, with an appropriate light source, such a translucent package can be used with an appropriate viewer to inspect the lens without details and variations of the light source induced by the package affecting such an inspection.

A more detailed description of the preferred embodiment of the illuminating system is given in copending U.S. application Ser. No. 994,388 filed Dec. 21, 1992 for Illumination System for Ophthalmic Lens Inspection.

Turning again to FIG. 2, shown is a further desirable characteristics of the present invention. In this figure, the package is shown after processing of the lens and inspection. In addition to the elements having like numerals in FIG. 1, the package is shown heat sealed with plastic-coated, metal foil 26 fused to raised annular sealing area 14, providing a hermetic seal. As shown, two packages of the present invention can be nested back-to-back. This is accomplished by having the distance between bowl 12 and second planar surface 16 sufficient to accommodate the bowl of a second package.

This type of nesting of pairs of packages permits storage of a number of packages within a secondary container in a minimal amount of space—a characteristic highly desirable with planned replacement contact lenses.

We claim:

1. A package containing an ophthalmic lens for inspection, processing and storage of the lens, said package comprising:

a substantially planar first surface, a concave bowl formed in said surface, said bowl having a radius of curvature sufficiently small to cause the lens to center therein by gravity, yet larger than the radius of curvature of the lens placed therein, said bowl having a depth less than the diameter of the lens contained therein, said bowl being translucent such that light transmitted through the bowl is substantially isotropic, imparting substantially no non-uniformity to the light source, a sealing area circumferentially about the circular boundary of the first planar surface and the concave bowl, and a sealing sheet substantially parallel with said first planar surface covering the concave bowl, thereby forming a cavity enclosing the lens placed therein, and hermetically sealed along said sealing area.

2. The package of claim 1 wherein the sealing area is a planar annulus raised above the first planar surface away from the concave bowl.

3. The package of claim 1 further comprising a second planar surface extending from an edge of the first planar surface at an angle greater than zero degrees and in the direction of the concave bowl.

4. The package of claim 3 wherein the second planar surface extends substantially the same distance from the first planar surface as the apex of the concave bowl such that the package rests level when placed on a flat, level resting surface.

5. The package of claim 3 further comprising a notch, said notch including a portion of the first planar surface, a portion of the second planar surface and the boundary therebetween sufficient to permit grasping of the sealing sheet for removal.

6. The package of claim 3 wherein the distance from the concave bowl to said second planar surface and said angle greater than zero degrees between said first and said second planar surfaces is sufficient to nest the bowl of a second package.

7. The package of claim 1 further comprising a plurality of projections substantially in a normal direction from the first planar surface and proximate an edge thereof for gripping of the package during opening.

8. The package of claim 1 wherein said bowl is constructed of a non-nucleated polymer such that when water is placed in said bowl the polymer surface is sufficiently wettable to substantially flatten the meniscus and optical aberrations therewith.

9. The package of claim 1 further comprising in said first planar surface, a means for indicating the presence and position of said package in a production line.

10. The package of claim 1 further comprising means for locating said package in a production line pallet.

11. The package of claim 10 wherein said means for locating said package in a production line carrying means is also used to indicate the presence and position of said package in a production line.

12. The package of claim 1 wherein the interior surface of the bowl has a roughness between 200 grit and 800 grit, sufficiently smooth to allow the lens to fall to the center of the bowl in water and to allow the lens to be slid against said interior surface for removal with a finger, but sufficiently rough to retain the lens during removal of water during the packaging process.

13. The package of claim 1 wherein the radius of curvature of the bowl is greater than 8.50 mm but less than 12.0 mm.

14. The package of claim 1 wherein the bowl contains a plurality of raised ribs located off-center of the bowl.

15. A package containing an ophthalmic lens for the storage and delivery of said lens, said package comprising:

a substantially planar first surface, a concave bowl formed in said surface, the interior surface of the bowl has a roughness less than 800 grit, allowing the lens to be slid against said interior surface for removal with a finger, while retaining the lens during removal of water during the packaging process, said bowl having a radius of curvature sufficiently small to cause the lens to center therein by gravity, yet larger than the radius of curvature and a depth less than the diameter of the lens contained therein, a sealing area circumferentially about the circular boundary of the first planar surface and the concave bowl, and a sealing sheet substantially parallel with said first planar surface covering the concave bowl, thereby forming an enclosed cavity, and hermetically sealed along said sealing area.

16. A package containing an ophthalmic lens for inspection, processing and storage of the lens, said package comprising:

a substantially planar first surface, a concave bowl formed in said surface, said bowl having a radius of curvature sufficiently small to cause the lens to center therein by gravity, yet larger than the radius of curvature of the lens placed therein, said bowl being translucent such that light transmitted through the bowl is substantially isotropic, imparting substantially no non-uniformity to the light source, a sealing area circumferentially about the circular boundary of the first planar surface and the concave bowl, and a sealing sheet substantially parallel with said first planar surface covering the concave bowl, thereby forming a cavity enclosing the lens placed therein, and hermetically sealed along said sealing area.

17. A package containing an ophthalmic lens for inspection, processing and storage of the lens, said package comprising:

a member having a substantially planar first surface and a substantially planar second surface, a concave bowl formed in said surface, said bowl extending in a first direction from said first surface and having a radius of curvature sufficiently small to cause the lens to center therein by gravity, yet larger than the radius of curvature of the lens placed therein, said bowl comprising a substantially hemispherical structure, said second surface extending in said first direction from an edge of the first surface at an angle between said surfaces greater than zero and less than 180 degrees, a sealing area circumferentially about the circular boundary of the first surface and the concave bowl, and a sealing sheet substantially parallel with said first surface covering the concave bowl, thereby forming a cavity enclosing the lens placed therein, and hermetically sealed along said sealing area.

18. The package of claim 17 wherein said bowl has a depth less than the diameter of the lens contained therein.

19. The package of claim 17 wherein the distance between the concave bowl and said second surface of the member is sufficient to accommodate the bowl of a similar package in a back-to-back nested fashion.

20. A package containing an ophthalmic lens for inspection, processing and storage of the lens, said package comprising:

a substantially planar first surface, a concave bowl formed in said surface, said bowl having a radius of curvature sufficiently small to cause the lens to center therein by gravity, yet larger than the radius of curvature of the lens placed therein, said first planar surface having a notch for indicating the presence and position of said package in a production line, a sealing area circumferentially about the circular boundary of the first planar surface and the concave bowl, and a sealing sheet substantially parallel with said first planar surface covering the concave bowl, thereby forming a cavity enclosing the lens placed therein, and hermetically sealed along said sealing area.

21. A package containing an ophthalmic lens for inspection, processing and storage of the lens, said package comprising:

a substantially planar first surface, a concave bowl formed in said surface, said bowl having a radius of curvature sufficiently small to cause the lens to center therein by gravity, yet larger than the radius of curvature of the lens placed therein, the bowl containing a plurality of raised ribs located off-center of the bowl the lens when centered in the bowl touching only the bowl center and not the ribs, a sealing area circumferentially about the circular boundary of the first planar surface and the concave bowl, and a sealing sheet substantially parallel with said first planar surface covering the concave bowl, thereby forming a cavity enclosing the lens placed therein, and hermetically sealed along said sealing area.

22. A package containing an ophthalmic lens for inspection, processing and storage of the lens, said package comprising:

a substantially planar first surface, a concave bowl formed in said surface, said bowl having a radius of curvature sufficiently small to cause the lens to center therein by gravity, yet larger than the radius of curvature of the lens placed therein, said bowl is constructed of a non-nucleated polymer such that when water is placed in said bowl the polymer surface is sufficiently wettable to substantially flatten the meniscus and optical aberrations therewith, a sealing area circumferentially about the circular boundary of the first planar surface and the concave bowl, and a sealing sheet substantially parallel with said first planar surface covering the concave bowl, thereby forming a cavity enclosing the lens placed therein, and hermetically sealed along said sealing area.

* * * * *